United States Patent [19]

Dudkowski

[11] 4,082,537

[45] Apr. 4, 1978

[54] 2,6-DINITROANILINE HERBICIDAL COMPOSITIONS

[75] Inventor: Joseph John Dudkowski, Bridgewater, N.J.

[73] Assignee: American Cyanamid Company, Stamford, Conn.

[21] Appl. No.: 780,377

[22] Filed: Mar. 23, 1977

[51] Int. Cl.$^2$ ............................................. A01N 17/00
[52] U.S. Cl. ................................. 71/121; 71/DIG. 1
[58] Field of Search ........................... 71/121, DIG. 1

[56] References Cited

U.S. PATENT DOCUMENTS

| | | | |
|---|---|---|---|
| 3,873,689 | 3/1975 | Frensch et al. | ............. 71/DIG. 1 X |
| 3,920,742 | 11/1975 | Lutz et al. | ................................ 71/121 |

*Primary Examiner*—Lewis Gotts
*Assistant Examiner*—Catherine L. Mills
*Attorney, Agent, or Firm*—H. G. Jackson

[57] ABSTRACT

The invention is a solid herbicidal composition comprising a molecular solution of sodium dialkyl $C_6$–$C_8$ sulfosuccinate or ethoxylated β-diamines in 2,6-dinitroanilines. The solution of the surfactant in the 2,6-dinitroaniline prevents formation of large crystals of the herbicides when in wettable powder form.

7 Claims, No Drawings

2,6-DINITROANILINE HERBICIDAL COMPOSITIONS

The broad spectrum herbicides of formula I, below, methods of preparation thereof, and their use as a highly effective preemergence herbicide for the control of undesirable plant species, are disclosed by A. W. Lutz et al. in U.S. Pat. No. 3,920,742 (1975).

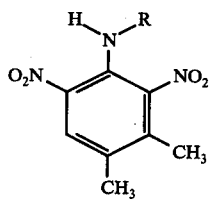

wherein R is 1-ethylbutyl, 1-ethylpropyl, 1-methylpropyl or 1-methylbutyl.

For use in agriculture, formula (I) herbicides may be advantageously formulated as a wettable powder. Wettable powders are usually prepared by grinding and milling the active ingredient with a solid carrier, such as attaclay, kaolin, diatomaceous earth, synthetic calcium silicate, fullers earth, talc, pumice, and the like. Usually, about 25% to 75% by weight of the active material, and from about 75% to 25% by weight of solid carrier, is used. In addition, there is generally added about 1% to 5% by weight of a dispersing agent, such as alkali metal salts of naphthalene sulfonic acid and anionic-nonionic blends, and from about 1% to 5% by weight of a surfactant, such as polyoxyethylene alcohols, acids, adducts, sorbitan fatty acid esters, sorbital esters, and the like. The amount of solid carrier is then reduced accordingly to compensate for the amounts of dispersing agent(s) and surfactant(s) incorporated into the formulation.

Wettable powders are usually dispersed in water and applied as dilute aqueous sprays at a rate of 0.28 kg to 22.4 kg/hectare of active ingredient to the area where control of undesirable plant species is desired.

A typical wettable powder containing N-(1-ethylpropyl)-2,6-dinitro-3,4-xylidine is represented by the following compositions:

| Component | Percent by Weight |
| --- | --- |
| N-(1-ethylpropyl)-2,6-dinitro-3,4-xylidine | 75.0 |
| Sodium salt of condensed naphthalene sulfonic acid | 1.0 |
| Sodium N-methyl-N-oleoyltaurate | 5.0 |
| Synthetic calcium silicate (quantity sufficient to 100%) | |
| | 100.0 |

The above components are blended and jet-milled to yield a wettable powder, containing 75% by weight of active material.

When this and similar formulations were evaluated in the greenhouse and in field trials, it was noted that freshly prepared wettable powders dispersed well in water and gave excellent preemergence control of undesirable plant species, irrespective whether the wettable powder was prepared from purified (recrystallized) or technical grade N-(1-ethylpropyl)-2,6-dinitro-3,4-xylidine. When, however, these samples were stored at ambient temperature for a period of time of two to three months, the aqueous dispersions prepared from the same samples showed that the active material tended to settle out rapidly and gave uneven control over the area treated. Some of these samples caused blockage of screens in the spray equipment, necessitating the dismantling and cleaning of the equipment.

Microscopic examination of the aqueous dispersions prepared from freshly prepared and aged wettable powders indicated that in the freshly prepared powders the aboveidentified herbicide is present in the form of a yellow, microcrystalline solid; whereas, in the aged samples, the same compound is present in the form of large orange crystals, 150 to 200 $\mu$m in size. These large crystals tend to settle out rapidly from the aqueous dispersions and may cause blockage of screens in spray equipment, and irregular distribution over the treated plots.

From the above data, it is surmised that the herbicide exists at ambient temperatures in the form of two distinct polymorphs: a yellow microcrystalline form and an orange macrocrystalline form; and that of the two, the latter appears to be the more stable polymorph. X-ray powder diffraction pattern data obtained on both types tends to confirm the above assumption. Apparently, in the course of the preparation of N-(1-ethylpropyl)-2,6-dinitro-3,4-xylidine, the yellow polymorph is obtained, which then slowly converts at ambient temperature to the more stable orange polymorph. Obviously, it would be of advantage if this conversion could be prevented, or at least slowed down considerably.

Surprisingly, we now find that if 1% to 1.5% by weight of sodium dioctyl sulfosuccinate [Chemical Abstracts. Sulfobutanedioic acid, 1,4-bis(2-ethylhexyl)ester sodium salt] is dissolved in molten N-(1-ethylpropyl)-2,6-dinitro-3,4-xylidine, the homogeneous melt is then cooled down until it solidifies, and is then used in the preparation of the aforesaid wettable powders; the thus-obtained wettable powders yield stable aqueous dispersions, and when stored, the dispersions prepared therefrom show the absence of the orange polymorph.

In general, a mixture of about 99% to about 98.5% by weight of N-(1-ethylpropyl)-2,6-dinitro-3,4-xylidine and about 1.0% to about 1.5% by weight of sodium dioctyl sulfosuccinate is stirred and heated at 56°-60° C. until a homogeneous melt forms. The melt is then poured in shallow containers and allowed to cool and solidify. The solid is then ground, and the thus-obtained solid herbicide/surfactant molecular solution is used for the preparation of the aforesaid wettable powders.

We also find that less than 1% by weight of the surfactant sodium dioctylsulfosuccinate present in the herbicide will not prevent the transition of the yellow polymorph to the undesired orange polymorph. Incorporation of 2%, or more by weight of the surfactant sodium dioctylsulfosuccinate in the herbicide, yields tacky solids which do not lend themselves well for the preparation of wettable powders.

It should be noted that if about 1% to about 1.5% by weight of sodium dioctyl sulfosuccinate is added during the preparation of wettable formulations (i.e., it is mechanically blended with the other components), it will not prevent the formation of the undesirable orange polymorph. Example 4, below, illustrates that surfactants of sodium dialkyl $C_6$-$C_8$ sulfosuccinate and ethoxylated $\beta$-diamines are effective surfactants of the invention.

The invention is further illustrated by the following non-limiting examples, below.

EXAMPLE 1

Preparation of Experimental Wettable Powders from N-(1-Ethylpropyl)-2,6-dinitro-3,4-xylidine, which has been fused with Sodium Dioctyl Sulfosuccinate Procedure A mixture of N-(1-ethylpropyl)-2,6-dinitro-3,4-xylidine (99.0 g) and sodium dioctyl sulfosuccinate (1.0 g) is stirred and heated until completely liquified. The melt is stirred for 15 minutes and then allowed to cool and solidify. By the above procedure, the following samples are prepared as shown in Table I below.

TABLE I

| Component | Experimental Wettable Powders | | |
|---|---|---|---|
| | 1 | 2 | 3 |
| N-(1-ethylpropyl)-2,6-dinitro-3,4-xylidine (Technical Grade) | | | |
| a. (92.3% real) | 99.0 | | |
| b. (92.8% real) | | 99.0 | |
| c. (91.4% real) | | | 99.0 |
| Sodium dioctyl sulfosuccinate (100% real) | 1.0 | 1.0 | 1.0 |
| Total weight in grams | 100.0 | 100.0 | 100.0 |
| Percent real | 91.4 | 91.4 | 90.5 |

Preparation of 75% wettable powders from the above samples

Procedure

The components of the blends are thoroughly mixed and are then jet-milled. In Table II, below, the composition of the wettable powders prepared is given.

TABLE II

Composition of Wettable Powders Containing 75% by Weight of N-(1-Ethylpropyl)-2,6-dinitro-3,4-xylidine

| Component | Wettable Powders 75% Real | | |
|---|---|---|---|
| | A | B | C |
| Table I. Sample 1. (91.4% real) | 41.0 | | |
| Table I. Sample 2. (91.4% real) | | 40.8 | |
| Table I. Sample 3. (90.5% real) | | | 41.4 |
| Sodium salt of condensed naphthalene sulfonic acid | 0.5 | 0.5 | 0.5 |
| Sodium N-methyl-N-oleoyltaurate | 2.5 | 2.5 | 2.5 |
| Synthetic calcium silicate | 6.0 | 6.2 | 5.6 |
| Total weight in grams | 50.0 | 50.0 | 50.0 |

The above prepared blends are examined by mixing 1.0 g of each with 99 ml of tap water in a 100 ml graduate cylinder, determining the time needed to fully wet out the powders and observing the aqueous dispersions obtained. The blends are then stored at ambient temperature. At two and five months storage, aqueous dispersions are prepared from each sample by the procedure described above, and the dispersions are examined under a microscope at 660X for the presence or absence of the undesirable, large, orange crystals. The data obtained are summarized in Table III, below.

TABLE III

| Table II Blend | Wetting Time in Seconds | Dispersion | | | Microscopic Examination at 660×, Full Field | |
|---|---|---|---|---|---|---|
| | | Initial | ½ Hour | 1 Hour | 2 Months | 5 Months |
| A | 14 | very good | very good, slight sediment | very good, slight sediment | no sign of large crystals | no sign of large crystals |
| B | 15 | very good | very good, slight sediment | very good, slight sediment | only two large crystals found in about 40 full fields | several 100 μm crystals |
| C | 8 | fair-good, slight flocculation | fair-good, 3 ml sediment | fair-good, 3 ml sediment | no sign of large crystals | no sign of large crystals |

By the above procedure, 100 pounds samples of N-(1-ethylpropyl)-2,6-dinitro-3,4-xylidine are fused with 1.25% by weight and 1.1% by weight of sodium dioctyl sulfosuccinate, respectively.

A 25 kg batch of 75% wettable powder is prepared from the sample containing 1.25% by weight of wetting agent, by the procedure described above and having the composition as given in Table II. After being stored at ambient temperature for three months, an aqueous dispersion (1 g wettable + 99 ml water) of the sample is examined at 660X and is found free of large, orange crystals. Similarly, a 100 g batch is prepared from the sample containing 1.1% by weight of wetting agent and stored at ambient temperature for two months. Examination (as shown) shows that the blend is free of large, orange crystals.

EXAMPLE 2

Evaluation of the Effect of the Amount of Sodium Dioctyl Sulfosuccinate Incorporated in N-(1-Ethylpropyl)-2,6-dinitro-3,4-xylidine in Preventing the Formation of the Undesirable Orange Polymorph By the procedures of Example 1, samples of N-(1-ethylpropyl)-2,6-dinitro-3,4-xylidine are fused with 1.0%, 0.5%, 0.25% and 0.1% by weight of sodium dioctyl sulfosuccinate, respectively, and then 50 g batches of wettable powders are prepared from each of the above samples. These wettable powders have the composition as given in Table II of Example 1.

The freshly prepared wettable powders are examined by dispersing 1.0 g each both in standard hard water (hardness = 345 ppm CaCO$_3$ equivalent) and tap water. The results obtained are summarized in Table IV below:

TABLE IV

| Concentration of Surfactant | Wetting Time in Seconds | Dispersion | | |
|---|---|---|---|---|
| | | Initial | ½ Hour | 1 Hour |
| 1.0% | 7 | good | 1 ml sediment | 2 ml sediment (total) |
| 0.5% | 13 | good | 0.5 ml sediment | 1 ml sediment (total) |
| 0.25% | 10 | good | 0.5 ml sediment | 0.5 ml sediment (total) |

TABLE IV-continued

| Concentration of Surfactant | Wetting Time in Seconds | Dispersion | | |
|---|---|---|---|---|
| | | Initial | ½ Hour | 1 Hour |
| 0.1% | 13 | good | slight sediment | 1 ml sediment (total) |

The wettable powders are then stored at ambient temperature for 2 months, fresh aqueous dispersions are prepared from each and examined under a microscope at 660X for the presence or absence of large orange crystals. Of the above samples, only the blend prepared from the herbicide containing 1% by weight of surfactant is found to be free of large orange crystals. All of the other samples show large orange crystals.

EXAMPLE 3

Preparation of a Wettable Powder wherein the Surfactant is Introduced into the Powder during the Blending Operation A wettable powder, containing 75% by weight of N-(1-ethylpropyl)-2,6-dinitro-3,4-xylidine and 1% by weight of sodium dioctyl sulfosuccinate (based on the weight of the above herbicide) is prepared by mixing and jet milling the components listed below:

| Component | Weight in Grams |
|---|---|
| N-(1-ethylpropyl-2,6-dinitro-3,4-xylidine (92% real) | 41.0 |
| Sodium salt of condensed naphthalene sulfonic acid | 0.5 |
| Sodium N-methyl-N-oleoyltaurate | 2.5 |
| Sodium dioctyl sulfosuccinate (85% real) | 0.5 |
| Synthetic calcium silicate | 6.0 |
| Total in grams | 50.0 |

The wetting time of the blend is 8 seconds, and a dispersion (1.0 g in 99 ml tap water) is very good. After two months storage at ambient temperature, the blend contains large orange crystals.

The above experiment clearly shows that addition of sodium dioctyl sulfosuccinate, 1% by weight based on the weight of N-(1-ethylpropyl)-2,6-dinitro-3,4-xylidine, in the course of the preparation of wettable powders does not prevent the formation of the undesirable orange polymorph.

EXAMPLE 4

Evaluation of the Effect of Various surfactants for the Prevention of the Formation of the Orange Polymorph in Wettable Powders Containing 75% by Weight of N-(1-ethylpropyl)-2,6-dinitro-3,4-xylidine Procedure Samples of N-(1-ethylpropyl)-2,6-dinitro-3,4-xylidine (92% real, 100 g each) are mixed with a surfactant (1% to 2% by weight, respectively) selected from those listed below; each mix is melted, is stirred a few minutes while molten, poured into shallow aluminum trays to cool and solidify. The thus-prepared samples are then used to prepare wettable powders by the procedure of Example 1, and having the composition as given in Table II of Example 1.

The following surfactants are evaluated:

a. Sodium dihexyl sulfosuccinate;
b. Tall oil ethoxylate;
c. Sodium diisopropyl naphthalene sulfonate;
d. Ethoxylated alkyl phenols;
e. Polyvinyl pyrrolidine (Average molecular weight: 10,000);
f. Nonylphenoxypoly(ethyleneethoxy)ethanol;
g. Dodecylphenoxypoly(ethyleneethoxy)ethanol;
h. Dialkylphenoxypoly(ethyleneethoxy)ethanol;
i. Octylphenoxypoly(ethyleneethoxy)ethanol;
j. Isopropyl myristate, melting point ~3° C;
k. Ethoxylated β-diamines; and
l. Ethoxylated β-amines.

The thus-prepared wettable powders are stored for three months at ambient temperatures, then dispersions (1.0 g sample in 99 ml water) are made of each and examined under a microscope at 660X for the presence or absence of large orange crystals. The data obtained are summarized in Table V below.

TABLE V

| Surfactant in Blends | Presence of Large Orange Crystals at Surfactant Concentration of | |
|---|---|---|
| | 1% | 2% |
| Control | yes | |
| a | yes | no |
| b | yes | yes |
| c | yes | yes |
| d | yes | yes |
| e | yes | yes |
| f | yes | yes |
| g | yes | yes |
| h | yes | yes |
| i | yes | yes |
| j | yes | yes |
| k | yes | no |
| l | yes | yes |

Results comparable to those in the Examples and Tables above are obtained with other 2,6-dinitroanilines of the invention.

I claim:

1. A solid herbicidal composition comprising a molecular solution of 1.0% to about 2.0% by weight of a surfactant of sodium dialkyl $C_6$–$C_8$ sulfosuccinate in about 98% to 99% by weight of a compound of the formula:

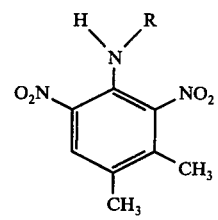

wherein R is 1-ethylbutyl, 1-ethylpropyl, 1-methylpropyl or 1-methylbutyl.

2. A composition according to claim 1 comprising a solution of about 1.0% to about 1.5% by weight of sodium dioctyl sulfosuccinate and about 99.0% to about 98.5% by weight of N-(1-ethylpropyl)-2,6-dinitro-3,4-xylidine.

3. A wettable powder herbicidal composition comprising from about 25% to about 75% of a solid solution of 1.0% to about 2% by weight of a surfactant of sodium dialkyl $C_6$–$C_8$ sulfosuccinate and about 98% to 99% by weight of a compound of the formula:

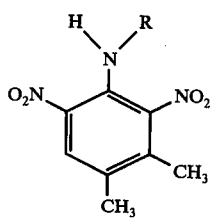

wherein R is 1-ethylbutyl, 1-ethylpropyl, 1-methylpropyl or 1-methylbutyl and from about 75% to about 25% of a solid carrier.

4. A herbicidal composition according to claim 3 wherein the surfactant is sodium dioctyl sulfosuccinate and the herbicide is N-(1-ethylpropyl)-2,6-dinitro-3,4-xylidine.

5. A herbicidal composition according to claim 4 wherein the solution comprises about 1.0% to 1.5% by weight of sodium dioctyl sulfosuccinate and about 99.0% to about 98.5% by weight of N-(1-ethylpropyl)-2,6-dinitro-3,4-xylidine.

6. A method of preventing the formation of crystals in wettable powder formulations of about 98% to 99% by weight of a compound of the formula:

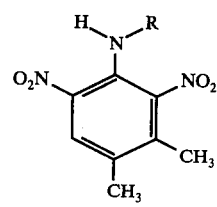

wherein R is 1-ethylbutyl, 1-ethylpropyl, 1-methylpropyl or 1-methylbutyl which comprises
　melting the compound at about its melting point,
　adding a surfactant of 1% to about 2% by weight of a sodium dialkyl $C_6$-$C_8$ sulfosuccinate,
　stirring the mixture until a homogeneous solution results, and then
　cooling the melt until it resolidifies.

7. A method of preventing the formation of crystals in wettable powder formulations of N-(1-ethylpropyl)-2,6-dinitro-3,4-xylidine according to claim 6 wherein about 99% to about 98.5% by weight of N-(1-ethylpropyl)-2,6-dinitro-3,4-xylidine is melted at 56°-60° C. and 1% to 1.5% by weight of sodium dioctylsulfosuccinate is added to the melt and the mixture is stirred at about 56°-60° C. for a sufficient period of time to obtain a homogeneous solution.

* * * * *